United States Patent
Guckenburger et al.

(10) Patent No.: US 8,460,166 B2
(45) Date of Patent: Jun. 11, 2013

(54) RADIOTHERAPY PLANNING AND DELIVERY

(75) Inventors: Matthias Guckenburger, Sutton (GB); Anthony Kavanagh, Sutton (GB); Kevin Brown, Horsham (GB)

(73) Assignees: Elekta AB (PUBL), Stockholm (SE); The Institute of Cancer Research, London (GB)

( * ) Notice: Subject to any disclaimer, the term of this patent is extended or adjusted under 35 U.S.C. 154(b) by 264 days.

(21) Appl. No.: 12/896,222

(22) Filed: Oct. 1, 2010

(65) Prior Publication Data
US 2012/0083681 A1 Apr. 5, 2012

(51) Int. Cl.
*A61N 5/10* (2006.01)

(52) U.S. Cl.
USPC .............................................. 600/1

(58) Field of Classification Search
USPC .................... 600/1–8, 300; 378/65
See application file for complete search history.

(56) References Cited

U.S. PATENT DOCUMENTS

| | | | | |
|---|---|---|---|---|
| 7,356,112 | B2 | 4/2008 | Brown et al. | 378/8 |
| 7,920,675 | B2 * | 4/2011 | Lomax et al. | 378/65 |

FOREIGN PATENT DOCUMENTS

| | | |
|---|---|---|
| EP | 1121957 A2 | 8/2001 |
| WO | WO 2005/025279 A1 | 3/2005 |
| WO | WO 2008/040379 A1 | 4/2008 |
| WO | WO 2010/066265 A1 | 6/2010 |

OTHER PUBLICATIONS

Berbeco, R., et al, "Residual motion of lung tumors in end-of-inhale respiratory gated radiotherapy based on external surrogates", *Medical Physics*, vol. 33, No. 11, Nov. 2006, pp. 4149-4156.
Borst, G., et al, "Radiation pneumonitis in patients treated for malignant pulmonary lesions with hypofractionated radiation therapy", *Radiotherapy and Oncology*, 91 (2009) pp. 307-313.
Engelsman, M., et al, "The effect of breathing and set-up errors on the cumulative dose to a lung tumor", *Radiotherapy and Oncology*, 60 (2001), pp. 95-105.
Engelsman, M., et al, "How much margin reduction is possible through gating or breath hold?", *Pyhsics in Medicine and Biology*, 50 (2005), pp. 477-490.
Fakiris, A., et al, "Stereotactic body radiation therapy for early-stage non-small-cell lunch carcinoma: four-year results of a prospective phase II study", *International Journal Radiation Oncology Biol. Phys.*, vol. 75, No. 3,(2009,) pp. 677-682.
Guckenberger, M., et al, "Four-dimensional treatment planning for stereotactic body radiotherapy", *International Journal Radiation Oncology Biol. Phys.*, vol. 69, No. 1, (2007), pp. 276-285.
Guckenberger, M., et al, "Influence of retrospective sorting on image quality in respiratory correlated computed tomography", *Radiotherapy and Oncology*, 85 (2007) pp. 223-231.

(Continued)

*Primary Examiner* — Samuel Gilbert
(74) *Attorney, Agent, or Firm* — Sunstein Kann Murphy & Timbers LLP

(57) ABSTRACT

Methods of radiotherapy planning and delivery are disclosed in which a radiation beam is directed towards a time-averaged mean position of the target during radiation-on. In addition, the radiation beam is gated to deliver radiation to the target only when the target is within a treatment volume centered on the mean position. Treatment plans according to embodiments of the present invention result in low doses to the surrounding healthy tissue, but high duty cycles and quicker treatment times.

14 Claims, 7 Drawing Sheets

OTHER PUBLICATIONS

Guckenberger, M., et al, "Pulmonary injury and tumor response after stereotactic body radiotherapy (SBRT): Results of a serial follow-up CT study", *Radiotherapy and Oncology*, 85 (2007), pp. 435-442.

Hanley, J., et al, "Deep inspiration breath-hold technique for lunch tumors: the potential value of target immobilization and reduced lung density in dose escalation", *International Journal Radiation Oncology Biol. Phys.*, vol. 45, No. 3 (1999), pp. 603-611.

Kaus, M., et al, "Assessment of a model-based deformable image registration approach for radiation therapy planning", *International Journal Radiation Oncology Biol. Phys*, vol. 68, No. 2 (2007) pp. 572-580.

Keall, P., et al, "Geometric accuracy of a real-time target tracking system with dynamic multileaf collimator tracking system", *International Journal Radiation Oncology Biol. Phys.*, vol. 65, No. 5 (2006) pp. 1579-1584.

Korreman, S., et al, "Respiratory gated beam delivery cannot facilitate margin reduction, unless combined with respiratory correlated image guidance", *Radiotherapy and Oncology*, 86 (2008), pp. 61-68.

McQuaid, D., et al, "IMRT delivery to a moving target by dynamic MLC tracking: delivery for targets moving in two dimensions in the beam's eye view", *Phys. Med. Biol.*, 51 (2006) pp. 4819-4839.

Ohara, K., et al, "Irradiation synchronized with respiration gate", *International Journal Radiation Oncology Biol. Phys.*, vol. 17 (1989), pp. 853-357.

Onishi, H., et al, "Hypofractionated stereotactic radiotherapy (HypoFXSRT) for state 1 non-small cell lung cancer: updated results of 257 patients in Japanese multi-institutional study", *Journal of Thoracic Oncology*, vol. 2, No. 7, Supplement 3, Jul. 2007.

Purdie, T., et al, "Cone-beam computed tomography for on-lne image guidance of lunch stereotactic radiotherapy: localization, verification, and intrafraction tumor position", *Int. J. Radiation Oncology Biol. Phys.*, vol. 68, No. 1 (2007), pp. 243-252.

Ricardi, U., et al, "Dosimetric predictors of radiation-induced lung injury in stereotactic body radiation therapy", *Acta Oncologica*, 48 (2009), pp. 571-577.

Ricardi, U., et al, "Sterotactic body radiation therapy for early state non-small cell lung cancer: results of a prospective trial", *Lung Cancer*, 68 (2010), pp. 72-77; www.elsevier.com/locate/lungcan.

Seppenwoolde, Y., et al, "Precise and real-time measurement of 3D tumor motion in lung due to breathing and heartbeat, measured during radiotherapy", *Int. J. Radiation Oncology Biol. Phys.*, vol. 53, No. 4 (2002), pp. 822-834.

Sibley, G., "Radiotherapy for patients with medically inoperable stage 1 nonsmall cell lung carcinoma", *Cancer*, Feb. 1, 1998, vol. 2, No. 3, pp. 433-438.

Sonke, J., et al, "Respiratory correlated cone beam CT", *Med. Phys.*, vol. 32 (4), Apr. 2005, pp. 1176-1186.

Sonke, J., et al, "Variability of four-dimensional computed tomography patient models", *Int. J. Radiation Oncology Biol. Phys.*, vol. 70, No. 2. (2008), pp. 590-598.

Sonke, J., et al, "Frameless stereotactic body radiotherapy for lung cancer using four-dimensional cone beam CT guidance", *Int. J. Radiation Oncology Biol. Phys.*, vol. 74, No. 22, (2009), pp. 567-574.

Timmerman, R., et al, "Stereotactic body radiation therapy for inoperable early stage lung cancer", *JAMA*, 2010;303(11); 1070-1076 (doi:10.1001/jama.2010.261).

Underberg, R., et al, "Benefit of respiration-gated stereotactic radiotherapy for stage I lung cancer: an analysis of 4DCT datasets", *Int. J. Radiation Oncology Biol. Phys.*, vol. 62. No. 2, (2005), pp. 554-560.

Vedam. S., et al, "Determining parameters for respiration-gated radiotherapy", *Medical Physics*, Vo. 28, No. 10, Oct. 2001, pp. 2139-2146.

Vedam, S., et al, "Determination of prospective displacement-based gate threshold for respiratory-gated radiation delivery from retrospective phase-based gate threshold selected at 4D CT simulation", *Medical Physics*, vol. 34, No. 11, Nov. 2007, pp. 4247-4255.

Wilbert, J. et al, "Tumor tracking and motion compensation with an adaptive tumor tracking system (ATTS): system description and prototype testing", *Medical Physics*, vol. 35, No. 9, Sep. 2008, pp. 3911-3921.

Wolthaus, J., et al, "Mid-ventilation CT scan construction from four-dimensional respiration-correlated CT scans for radiotherapy planning of lung cancer patients", *Int. J. Radiation Oncology Biol. Phys.*, vol. 65 No. 55 (2006), pp. 1560-1571.

Wolthaus, J., et al, "Reconstruction of a time-averaged midposition CT scan for radiotherapy planning of lung cancer patients using deformable registration", *Medical Physics*, vol. 35, No. 9, Sep. 2008, pp. 3998-4011.

Wolthaus, J., et al, "Comparison of different strategies to use four-dimensional computed tomography in treatment planning for lung cancer patients", *Int. J. Radiation Oncology Biol. Phys.*, vol. 70, No. 4 (2008), pp. 1229-1238.

European Patent Office, Officer Beck, European Search Report, EP 11007912, date of completion Feb. 1, 2012, 4 pages.

* cited by examiner

RADIOTHERAPY PLANNING AND DELIVERY

FIELD OF THE INVENTION

The present invention relates to radiotherapy, and particularly to methods and apparatus for planning and delivering radiotherapeutic treatment to a target undergoing cyclical movement within a patient.

BACKGROUND ART

A number of different methods for reducing the radiation dose to healthy tissue while maintaining the dose to the target during radiotherapy treatment exist. In the case of targets which undergo cyclical motion due to physiological movements of the patient, such as breathing, the sparing of healthy tissue is more complicated. There are various existing techniques to deal with moving targets. One approach is to gate the radiation, i.e. only allow the radiation beam to be active when the target is in an optimal position for treatment. In an alternative approach, the treatment beam may be widened to encompass the entire range of target positions, such that the target is continuously irradiated throughout its course of motion. In a yet further approach, the treatment beam may be continuously active, but targeted only at the average position of the tumour with the treatment beam(s) not fully encompassing the entire range of target positions.

Each of the previously mentioned techniques has its own drawbacks. Increasing the beam size to cover the entire range of motion obviously increases the amount of healthy tissue that will be exposed to radiation during the course of treatment. Although the target is continuously irradiated in this approach, the surrounding healthy tissue is also irradiated for a very large part of the movement cycle. Targeting the average tumour position reduces the dose applied to healthy tissue relative to the previous approach, but still more healthy tissue is exposed than is ideal.

Gating further reduces the amount of healthy tissue irradiated, and results in the least amount of healthy tissue irradiated of the three approaches described above. However, this requires that the beam is turned off for large periods of time during the treatment, leading to increased treatment times and lower patient throughput.

What is needed is a technique that combines the advantages of these techniques, with reduced disadvantages.

SUMMARY OF THE INVENTION

The inventors of the present invention have found that a method combining targeting the mean position of the tumour together with gating of the radiation beam, leads to a reduction in irradiated healthy tissue compared to approaches treating the entire motion range or just using the mean position (and minimal increase compared to just gating the radiation). Surprisingly, the inventors have also found that a substantial reduction in the time taken to deliver the treatment is achieved compared to gating alone, with minimal increase in time compared to the two "beam always on" alternatives.

In a first aspect of the invention, therefore, there is provided a method of treating a target undergoing cyclical motion within a patient. The method comprises directing a source of therapeutic radiation towards a time-averaged mean position of the target; and gating the source of therapeutic radiation to deliver radiation only when the target is within a treatment volume centred on the time-averaged mean position, the treatment volume having a relevant dimension smaller than the magnitude of the cyclical motion.

In a second aspect of the present invention, there is provided a method of generating a radiotherapy treatment plan for a target undergoing cyclical motion within a patient. The method comprises determining a time-averaged mean position of the target; and calculating a treatment plan in which a source of therapeutic radiation is directed at the time-averaged mean position of the target, and in which the source of therapeutic radiation is gated to deliver radiation only when the target is within a treatment volume centred on the time-averaged mean position, the treatment volume having a relevant dimension smaller than the magnitude of the cyclical motion.

In either of the above methods, the treatment volume dimension may be equal to the diameter of the target plus a safety margin. For static targets, a safety margin combines the uncertainty in the definition of the target and residual uncertainty in the placement of the radiation in the patient. This is known, and efforts have been directed to reducing this safety margin by better characterisation of the target shape and location, and by better definition and control of the beam. This invention seeks to address the problem of a target affected by breathing motion, and proposes that we increase the safety margin by an additional amount associated with this breathing motion.

In embodiments, the safety margin may be at most 15 mm, or at most 10 mm.

The treatment plan may be generated by first setting the safety margin at a particular value; and then adapting a duty cycle of the source of therapeutic radiation to achieve satisfactory irradiation of the target. Alternatively, it may be generated by first setting a duty cycle of the source of therapeutic radiation; and then adapting the safety margin to achieve satisfactory irradiation of the target.

The method of generating a treatment plan may be embodied on a computer program product, for execution on a computer. Thus, in a third aspect, there is provided a computer program product comprising executable code for performing the method of generating a treatment plan as set out above.

There is (of course) no reason why the gating window should be constant with angle. Any movements in the left/right or anterior/posterior direction will tend to be negated at certain gantry angles. As such, the effective motion within the field of view of the beam is reduced, and hence could duty cycle could go up. Thus, according to the invention the "cyclical motion" could be the movement of the target in absolute terms or (preferably) the movement of the target in the field of view of the beam.

BRIEF DESCRIPTION OF THE DRAWINGS

An embodiment of the present invention will now be described by way of example, with reference to the accompanying figures in which.

DETAILED DESCRIPTION OF THE EMBODIMENTS

As described above, there are particular difficulties in treating targets (e.g. tumours) within a patient which undergo cyclical motion due to some physiological movement. The cyclical motion which is most frequently relevant in this regard is that due to the respiratory cycle, i.e. expansion and contraction of the lungs as the patient breathes. The following description is therefore primarily concerned with the respiratory cycle, in which the patient's breathing is monitored and the location of the target throughout the respiratory cycle determined. However, those skilled in the art will fully appreciate that the principles described herein are equally applicable in compensating for target motion due to other physiological cycles, such as the cardiac cycle, for example.

The inventors have found that, in general, a treatment plan in which the therapeutic radiation is directed at a time-averaged position of the target but also gated to reduce the effective motion of the target relative to the radiation beam has surprising benefits when compared to prior art treatment plans. That is, the therapeutic radiation beam is kept pointing towards a time-averaged position of the target over the cycle. In practice, the beam may rotate around the patient, but its isocentre is kept at the time-averaged mean position. In addition, the radiation beam is enabled only when the target is within a treatment volume centred on the time-averaged position. At extremes of the target motion, when it lies outside the treatment volume, the radiation beam is disabled to reduce the dose applied to healthy tissue away from the target.

Figure 1:
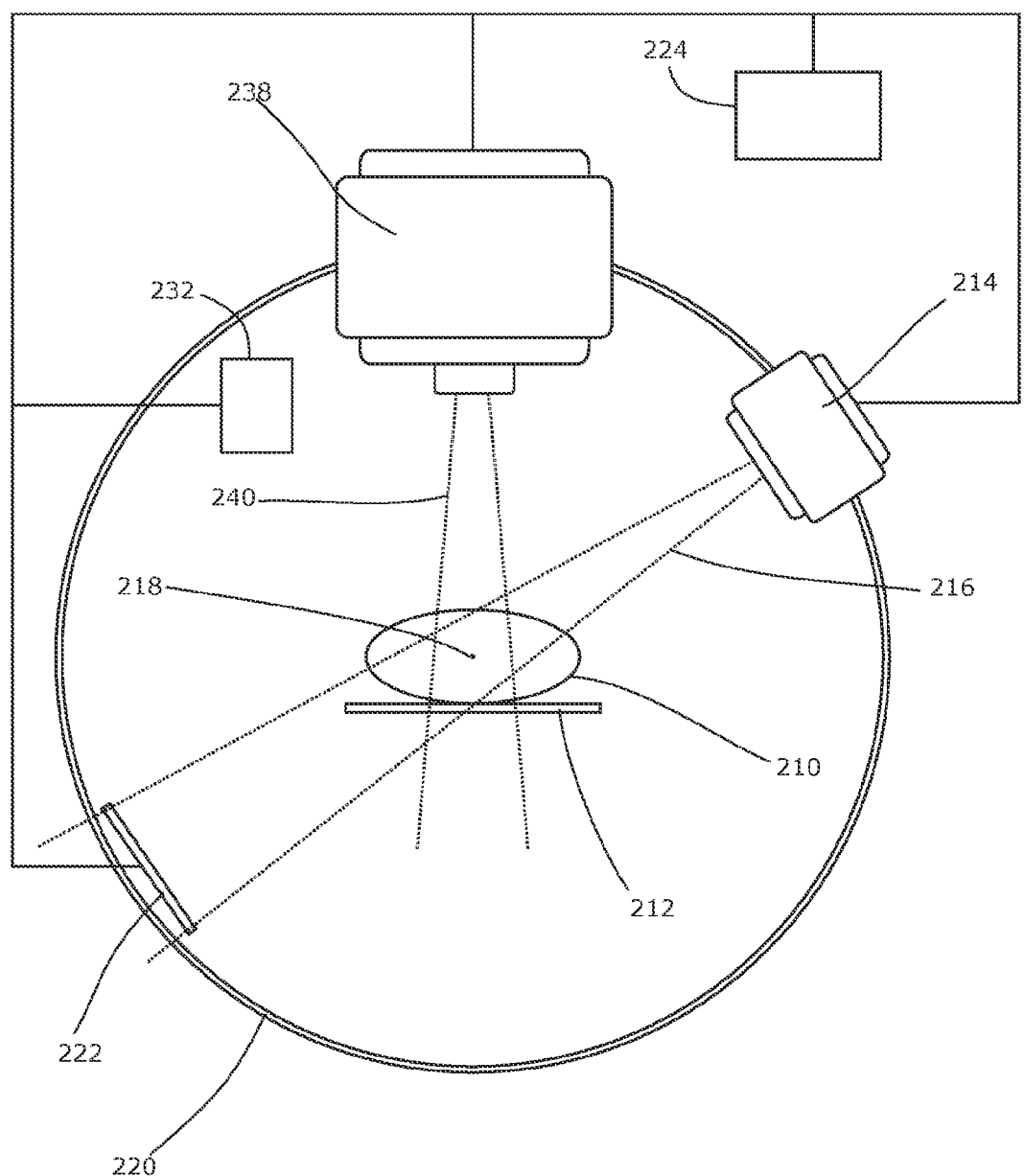
FIG. 1 is a schematic drawing showing a radiotherapy apparatus according to embodiments of the present invention.

The invention can be performed using a radiotherapeutic apparatus such as is known in the art. FIG. 1 shows one such apparatus.

A patient 210 is supported on a couch 212 which may be of any suitable design. Couches typically allow the elevation, lateral and longitudinal position of the patient to be adjusted, and this may be provided for as desired.

An x-ray source 214 is arranged to project a wide beam 216 of radiation generally directed towards the isocentre 218 of the patient. The source 214 is rotatable around the isocentre 218 on a rotational support 220. The support can, for example, be in the form of a ring or annulus around the patient 210 and couch 212 in which the source is mounted, or it can be a C-arm, or any suitable support allowing the source to rotate, or any combination thereof.

A two-dimensional flat-panel detector 222 is also mounted on the support 220, opposite the source 214 and arranged to rotate in synchronism therewith. If the support includes a C-arm then this can be achieved by mounting the detector on the opposite arm.

Thus, radiation emitted by the source 214 is partially absorbed by the patient and the attenuated signal is detected by the flat panel detector 222. The source 214 and detector 222 are then indexed rotationally and a fresh image obtained. This is repeated until sufficient images are acquired to reconstruct the volume data, typically one complete rotation.

The apparatus further comprises cables linking the source 214, detector 222 and rotational support 220 to a controller 224 which processes the data generated including the images, source intensity (etc), and rotational support position. Data is output via any suitable means, for example a monitor but not limited thereto, and the system is controlled by any suitable input means, for example a keyboard, but likewise not especially limited thereto.

We have found that there are artefacts in the reconstructed volume data of cone beam CT systems, which we have traced to patient breathing movements. To overcome or alleviate these, respiration correlation techniques are applied to the acquired projection images by the controller 224. Further details on this process can be found in FIG. 7, below, or in our earlier U.S. application Ser. No. 12/870,256 and our earlier PCT application WO 2010/066265.

To assist in this process, a surrogate signal acquisition system is provided at 232. Various surrogate signals may be used, and all are within the scope of the present invention. Examples include the Varian RPM system, in which an external marker on the surface of the patient is monitored by a camera, the VisionRT camera-based surface tracking system, the Accuray system using a marker vest and cameras, and our use of a pressure sensor in the abdominal compression plate (see WO2008/040379). The surrogate signal will usually be one having a low latency, to allow it to be used for gating the radiation beam or tracking the target position.

The apparatus further comprises a therapeutic source of radiation 238 controlled by the controller 224, and arranged to emit a suitably collimated beam of therapeutic radiation 240.

Figure 2:
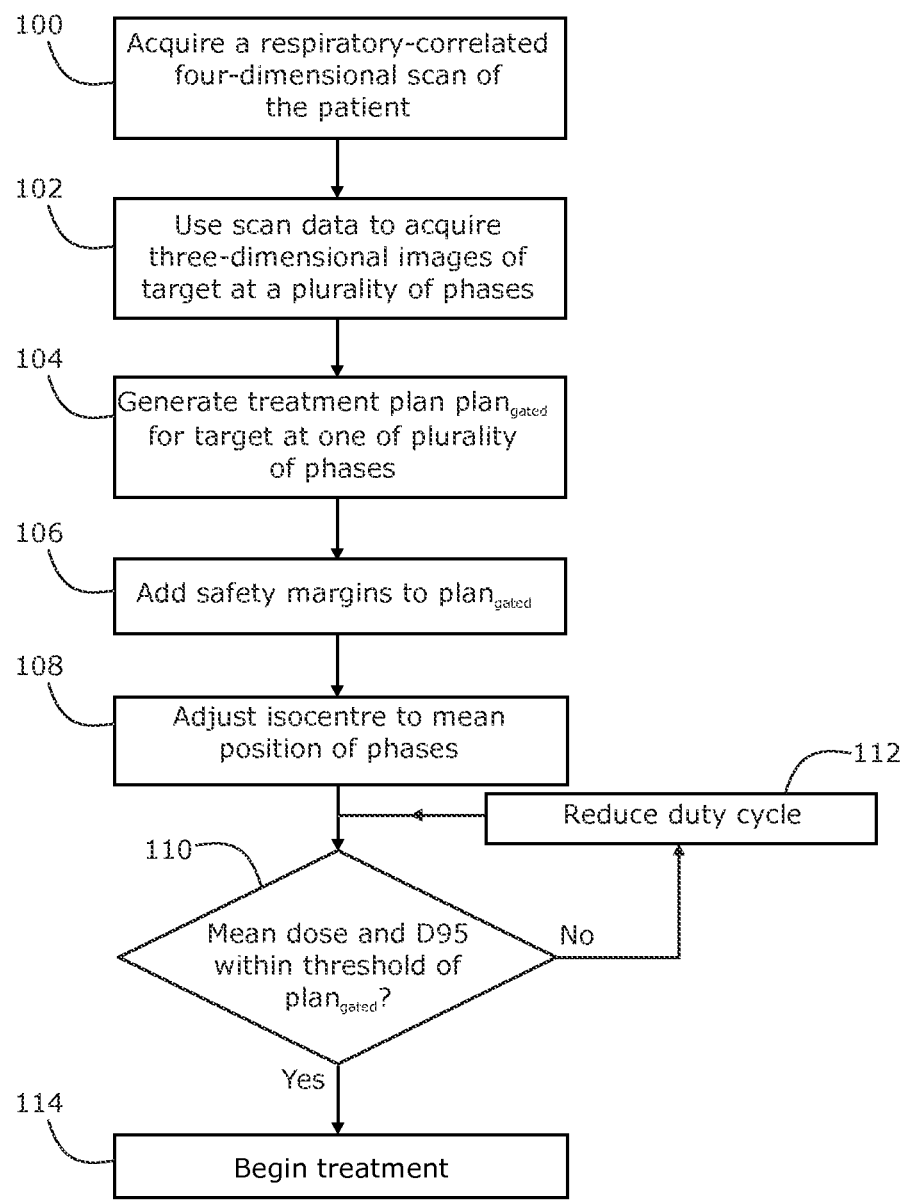
FIG. 2 is a flowchart of a method according to embodiments of the present invention.

FIG. 2 is a flowchart of a method of generating such a treatment plan, according to an embodiment of the present invention.

The process begins in step 100, in which a four-dimensional scan is performed of the target area in the patient, i.e. an area within the patient containing at least the target for treatment, as well as possibly surrounding tissue and anatomical structures. In step 102, the scan data is used to generate/reconstruct three-dimensional images of the target area at a plurality of phases in the cycle. Further details on these two steps can be found in FIG. 7 and the associated description.

In step 104, a treatment plan "$plan_{gated}$" is developed for the target as shown in one of the images, i.e. at one phase of its cyclical motion. Although any phase can be selected, in practice the movement of the target at the end of exhalation is likely to be slowest. Therefore the image of the target area corresponding to a phase nearest the end-exhalation phase may be chosen in one embodiment.

The treatment plan "$plan_{gated}$" is generated to have a duty cycle (i.e. the percentage or fraction of time the radiation beam is enabled) which is very low, e.g. 12.5% in one embodiment. The low duty cycle means that, during radiation beam on-time, the movement of the target is minimal.

The characteristics of the treatment plan "$plan_{gated}$" are determined and act as a reference for future treatment plans. Such characteristics may include, for example, standard parameters such as the maximum clinical target volume (CTV) dose, the mean CTV dose, the total dose received by 95% of the CTV (the D95), and the dose(s) delivered to organs-at-risk.

In step 106, minimal additional breathing safety margins are added to the treatment plan $plan_{gated}$. For target motions less than 10 mm to 15 mm it has been found that the mean tumor position concept without gating provided adequate irradiation of the target by including minimal additional breathing safety margins of about 2 mm.

In step 108, an updated treatment plan is generated from the original plan $plan_{gated}$ with safety margins. The isocentre is adjusted to the mean position of the target over the plurality of images created in step 102, instead of its previous position based on just one of the phases. In addition, the duty cycle is increased to 100%, i.e. the radiation beam is enabled all of the time. The characteristics of this updated treatment plan are then calculated, i.e. the mean dose to the CTV and the D95 as before.

In step 110, the characteristics of the updated treatment plan are compared with the characteristics of the original gated plan plan$_{gated}$. If the characteristics are within a threshold of those of plan$_{gated}$, the treatment plan is approved and treatment can begin based on the approved treatment plan (step 114). The threshold may be an absolute threshold or a relative threshold (e.g. 2%).

If the characteristics are not within the threshold, the process moves to step 112, in which the duty cycle is reduced by an incremental amount (e.g. 5%), and the characteristics of this new treatment plan are calculated. It is most efficient if the duty cycle is reduced by eliminating times when the target is at a position with the longest distance to the mean position. These times can be seen by referring to the position of the target in the plurality of phases. Once these times have been eliminated is will be obvious that the mean target position during radiation on-time will need to be recalculated and used in subsequent steps. The process moves back to step 110, where the characteristics are compared with those of plan$_{gated}$. This control loop repeats until an acceptable treatment plan is found.

Thus the method iteratively calculates a treatment plan which is centred on the time-averaged mean position of the target during radiation on-time, where the radiation beam is gated to deliver radiation only when the target is within a treatment volume. In some cases, where the magnitude of cyclical motion is particularly low, the radiation beam may not be gated at all; that is, the radiation beams operates at a duty cycle of 100%. However, where the magnitude of cyclical motion is significant (e.g. over 10 mm or over 15 mm), the radiation beam is gated to reduce the effective motion of the target (i.e. the motion during radiation on-time) to 10 mm or 15 mm or below.

Figure 3:
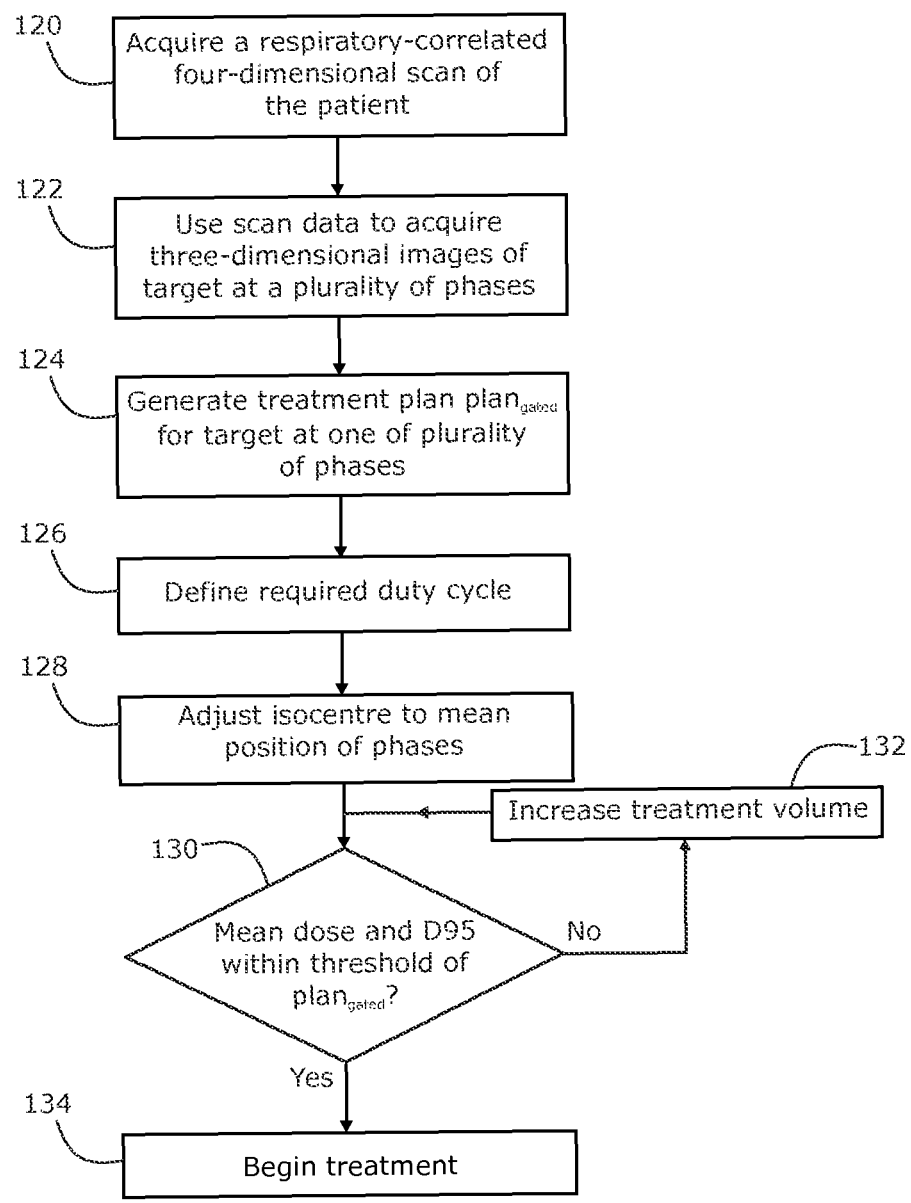
FIG. 3 is a flowchart of a method according to alternative embodiments of the present invention.

FIG. 3 is a flowchart of a method for generating a treatment plan according to alternative embodiments of the present invention in which, instead of defining safety margins around the target and calculating an appropriate duty cycle, the duty cycle is defined and the safety margins are calculated.

The first few steps are the same as shown in FIG. 2. Thus, the method begins in step 120, in which a four-dimensional CT scan is taken of the area surrounding the target. A plurality of images are generated from the scan data, corresponding to the target area at a plurality of phases in the respiratory cycle (step 122). On the basis of one of these images (e.g. the phase nearest the end-exhalation point of the cycle), a treatment plan plan$_{gated}$ is generated, with a duty cycle sufficiently short that movement of the target is minimized (step 124).

The method now differs from that shown in FIG. 2. A required duty cycle is defined in step 126. The duty cycle parameter is associated with the overall length of time required to treat the patient, i.e. to achieve the dose prescribed by the physician. A higher duty cycle results in faster treatment, while a shorter duty cycle increases treatment time. Thus this embodiment may be useful in shortening the overall treatment time, resulting in reduced intra-fractional patient motion and (consequently) increased accuracy of treatment. In addition, the invention can help where the treatment time is pre-determined. For example, the demands on a radiotherapy machine are usually such that it is almost constantly in use. For that reason, each treatment session may not be allowed to exceed a particular duration and therefore the duty cycle may be set with that in mind.

In step 128, the treatment plan plan$_{gated}$, updated with the required duty cycle, is moved so that the isocentre is positioned on the time-averaged mean position of the target. The safety margin is set so that the target lies within the treatment volume throughout its cycle of motion. The characteristics of this updated treatment plan are then calculated (e.g. mean dose to CTV, D95, etc).

In step 130, those characteristics are compared with the characteristics of plan$_{gated}$. If the characteristics are within a threshold of the plan$_{gated}$ characteristics, the plan is approved and treatment can begin (step 134). If the characteristics fall outside the threshold, the process moves to step 132, where the safety margins are increased. The characteristics of this further updated treatment plan are updated and the process moves back to step 130. Thus, the control loop repeats until acceptable safety margins have been reached.

In practice, the inventors have found that cases where the target motion has a magnitude below about 10 or 15 mm and minimal breathing safety margins are used, this can be adequately treated with a full (i.e. 100%) duty cycle. Where the cyclical motion is greater than that, the "effective" motion needs to be reduced to below 10 to 15 mm by gating the radiation beam. That is, the motion of the target during radiation on-time can be reduced to below 10 or 15 mm by gating the beam; otherwise larger safety margins would be necessary.

Figure 4:
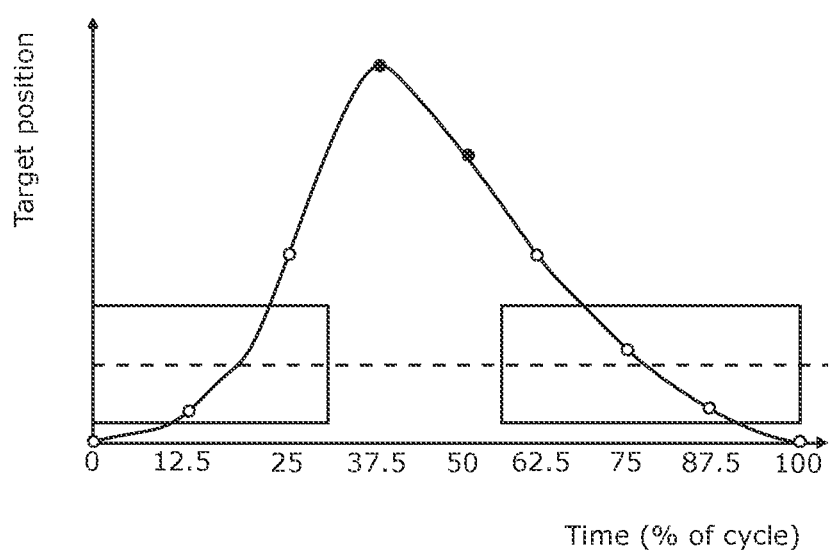
FIG. 4 is a schematic graph showing an example of a treatment plan according to embodiments of the present invention.

An example of the treatment plan resulting from these processes is shown in FIG. 4.

The x-axis is the time as a percentage of a single cycle. The y-axis shows the displacement of the target along a particular direction. The circles indicate the target position in each of the images obtained from the four-dimensional scan, and the line connecting them is a schematic illustration of the line of best fit. The dashed line indicates the time-averaged mean position of the target during radiation on-time. The rectangles indicated the timing and positioning of the radiation beam. As can be seen, the radiation beam is centred on the mean position of the target.

Where the circles (data points) are black, the target falls outside the treatment volume and the radiation beam is disabled; where they are white, the radiation beam is enabled, i.e. the target falls within the safety margins defined or calculated as part of the treatment plan. Note that the target need not actually fall within the path of the radiation beam to be within the treatment volume; the radiation beam is enabled for certain phases even though the target is positioned outside the radiation beam itself.

Figure 5:
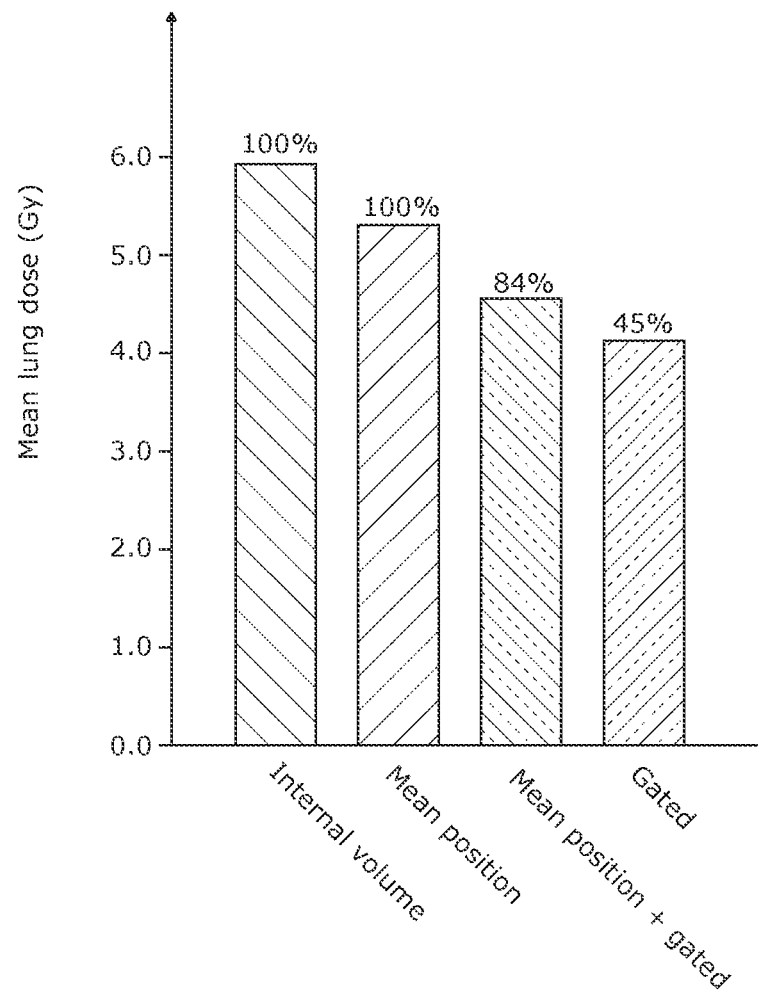
FIG. 5 is a graph showing experimental data.

FIG. 5 is a bar chart showing experimental data for four alternative treatment plans, collated from a group of patients with an average motion amplitude of 19 mm in the cranio-caudal direction. The y-axis represents the mean dose to the lungs, and the duty cycle calculated for each treatment plan is shown above each bar.

The "internal volume" plan is a treatment plan in which the 80% isodose line encompasses the internal target volume of the target motion. The internal target volume was generated by combining the clinical target volume of the target in each of the four-dimensional CT images. The radiation beam in this plan is enabled all of the time, i.e. a duty cycle of 100%.

The "mean position" plan is a treatment plan in which the 80% isodose line encompasses the clinical treatment volume at its time-averaged mean position, plus safety margins. In this plan, the radiation beam is also enabled for 100% of the time.

The "mean position+gated" plan is a treatment plan generated according to the method shown in FIG. 2. The method of FIG. 3, however, would also generate a similar plan.

The "gated" plan is a treatment plan generated according to steps 100, 102 and 104, for example, as described above.

For each of the treatment plans, the dose is normalized to provide the same dose to the clinical target volume. A higher dose on the y-axis therefore represents a higher dose to the surrounding, healthy tissue (in this case, the lungs). As previously explained, a higher duty cycle is associated with shorter treatment times.

As expected, the internal volume plan results in the highest dose to the lungs. This is reduced by targeting the time-averaged mean position, but the dose to the lungs is still relatively high. The gated plan results in the lowest dose to the lungs, but the duty cycle of 45% results in the treatment time being extended by more than a factor of 2, which makes it somewhat long.

The "mean position+gated" plan according to embodiments of the present invention provides a marked reduction in the dose to the lungs, nearly as much as the gated plan. In addition, however, the calculated duty cycle is still relatively high at 84%. Thus the dose to the healthy tissue is reduced, but the treatment time only increased by less than 20%. It is surprisingly found that treatment plans according to embodiments of the present invention enjoy the majority of the benefits of pure gated and mean position plans, whilst suffering from reduced drawbacks.

Figure 6:
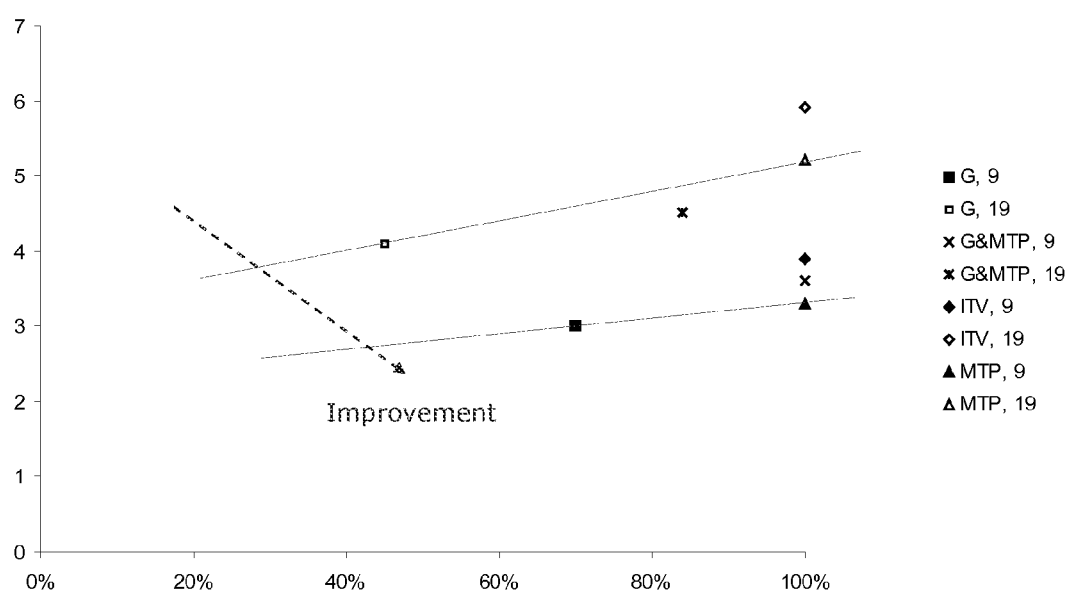
FIG. 6 is a further graph showing experimental data.

FIG. 6 is a plot of the mean lung dose versus the duty cycle for each of the four plans described above, and for two patient groups: one having an average target motion amplitude of 9 mm, and one having an average target motion amplitude of 19 mm. The four plans are "gated" (G), "gated+mean target position" (G&MTP), "internal target volume" (ITV) and "mean target position" (MTP). As shown by the dashed line and arrow, it is generally desirable for the points to be positioned as far as possible to the lower right of the graph, as this represents high duty cycle (i.e. fast treatment times) and low mean dose (i.e. dose to healthy tissue).

The results for the 19 mm patient group are generally positioned at higher mean doses. This is to be expected, given the greater movement of the target. A straight line has been plotted, indicating an approximate indication of the balance achieved between these two factors by the conventional treatment plans "gated" and "mean target position". The treatment plan according to embodiments of the invention, "G&MTP", is positioned lower and to the right of this line. Thus the treatment plan results in a plan which has an improved balance between treatment time and dose to healthy tissue than would ordinarily be expected, at least for patients in which the target has a relatively large amplitude of motion.

The results for the 9 mm patient group are positioned lower, and again a straight line gives an approximate indication of the balance achieved between the two factors, for the conventional treatment plans "gated" and "mean target position". Although the treatment plan according to embodiments of the invention results in a higher mean dose in these patients, it is not significantly worse. Indeed, as no gating was required for these patients (in view of the small movement), the mean target position concept with 100% duty cycle was sufficient (and this result is therefore to be expected).

Thus the present invention provides a method of treatment and a method of generating treatment plans in which certain target motions (especially those involving large amplitudes) can be treated faster and with less severe side-effects than previously. Other target motions can also be treated with similar results to conventional treatment plans.

Figure 7:
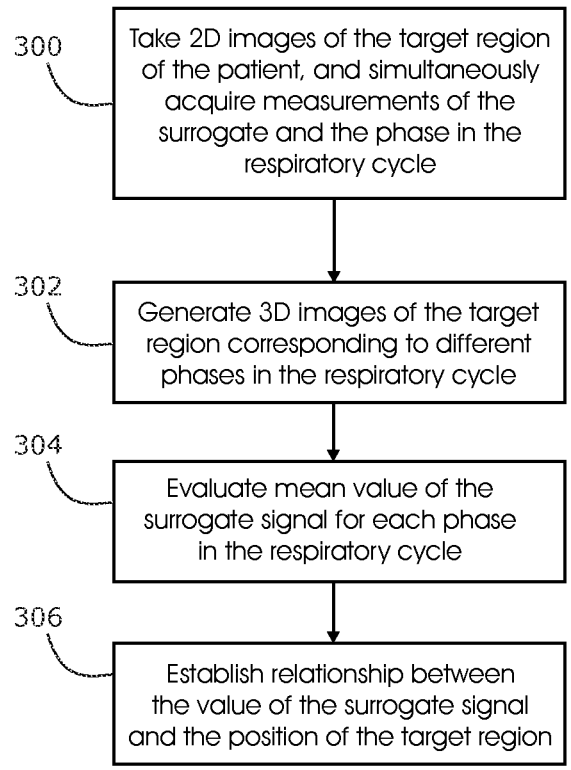
FIG. 7 is a flowchart of a method of acquiring four-dimensional CT scan of the target area, according to an embodiment of the present invention.

FIG. 7 shows the substeps of a method to generate four-dimensional images of the target area, grouped according to the phase in the respiratory cycle.

In step 300, the patient is placed in the position required for treatment and a CT scan of the region of interest is taken. This involves acquiring a series of projection images, i.e. a plurality of 2D x-ray images of the region taken from a range of different directions as the imaging head rotates around the patient. Typically, this rotation is about the cranio-caudal axis of the patient.

As each image is acquired, the value of a surrogate signal to be calibrated is recorded and stored in a manner associated with the image. Various surrogate signals may be used, as discussed above.

Each image is then assigned a breathing phase; our preferred way of doing so at present is to analyse the features in the image as set out in our earlier U.S. Pat. No. 7,356,112; that document is therefore incorporated herein by reference and readers are alerted that a reading of that document is essential to a thorough understanding of the present invention. A feature in the image such as the position of the diaphragm provides a suitable indicator of breathing phase. Other features in the image or other methods of determining breathing phase can be employed, however.

Once each image has been allocated a phase, they can be allocated to a suitable group of images consisting of images with like (i.e. similar) phase. Separate three-dimensional CT reconstructions are then obtained from each group (step 302); each CT reconstruction therefore provides a high quality three-dimensional image of the patient structure at a specific point in the breathing cycle.

After reconstruction is completed, the target position is determined in each reconstruction, i.e. in each breathing phase. This position can be identified manually by a clinician in each reconstruction, or having identified the position in one reconstruction the position in all other reconstructions can be determined by automated (or semi-automated) analysis of the reconstructions.

The above two steps are thus sufficient for the purposes of treatment planning in steps 100, 102, 120 and 122. However, the method can be extended to provide an indication of the target position during treatment.

The value of the surrogate associated with each of the images that contributed to each reconstruction is, of course, already known and recorded. This means that a relationship between the target position and the surrogate value can be plotted and analysed.

Thus, the mean value of the surrogate can be calculated for each breathing phase (step 304), and hence for each of a certain number of target positions. More usefully, this data can be used to calculate the most likely position of the target for any given value of the surrogate (step 306). This most likely value can be used to drive the gating system 224 and so control the therapeutic radiation appropriately during treatment.

The above deals with the treatment planning aspects of the invention. The treatment plan can then be delivered to the patient, using the apparatus described above.

The work-flow for this will be similar to the planning process. The planning was been performed to achieve a particular margin (with adjustment of the duty cycle) or to achieve a particular duty cycle (with adjustment of the safety margins). Both approaches to planning result in a particular residual motion of the target.

The patient is then set in place, targeting the mean target position at the isocentre. The appropriate gating window (duty cycle) is then applied during treatment, which could be done as follows;

1) using the identical duty cycle as planned
2) using IGRT (image-guided radiation therapy) with adaptation of the duty cycle to achieve the same residual motion as in treatment planning (for example, if motion of the target has changed compared to that during treatment planning)
3) using continuous monitoring of the target motion and dynamic adjustment of the duty cycle (if motion of the target is highly irregular)

The present invention thus provides methods of generating a treatment plan for radiotherapy, and of treating a patient using radiotherapy, in which the radiation dose applied to healthy tissue is reduced compared to "beam always on" treatment plans, but in which the duty cycle is much higher than pure gated treatment plants.

It will of course be understood that many variations may be made to the above-described embodiment without departing from the scope of the present invention.

The invention claimed is:

1. A method of treating a target undergoing cyclical motion within a patient, the method comprising:
    directing a source of therapeutic radiation towards a time-averaged mean position of the target; and
    gating the source of therapeutic radiation to deliver radiation only when the target is within a treatment volume centred on the time-averaged mean position, the treatment volume having a relevant dimension smaller than the magnitude of the cyclical motion.

2. The method as claimed in claim 1, wherein the treatment volume dimension is equal to the diameter of the target plus a safety margin.

3. The method as claimed in claim 2, wherein the safety margin is at most 15 mm.

4. The method as claimed in claim 3, wherein the safety margin is at most 10 mm.

5. A method of generating a radiotherapy treatment plan for a target undergoing cyclical motion within a patient, the method comprising:
    determining a time-averaged mean position of the target; and
    calculating a treatment plan in which a source of therapeutic radiation is directed at the time-averaged mean position of the target, and in which the source of therapeutic radiation is gated to deliver radiation only when the target is within a treatment volume centred on the time-averaged mean position, the treatment volume having a relevant dimension smaller than the magnitude of the cyclical motion.

6. The method as claimed in claim 5, wherein the treatment volume dimension is equal to the diameter of the target plus a safety margin.

7. The method as claimed in claim 6, further comprising:
    setting the safety margin at a particular value; and
    adapting a duty cycle of said source of therapeutic radiation to achieve said safety margin.

8. The method as claimed in claim 6, further comprising:
    setting a duty cycle of said source of therapeutic radiation; and
    adapting the safety margin to achieve said duty cycle.

9. The method as claimed in any one of claims 5 to 8, wherein the safety margin is at most 15 mm.

10. The method as claimed in claim 9, wherein the safety margin is at most 10 mm.

11. A computer program product for generating a radiotherapy treatment plan to treat a target undergoing cyclical motion within a patient, the treatment plan to be put into effect by a radiotherapy apparatus having a source of therapeutic radiation, the computer program product comprising code which, when executed on a computer, controls the computer to:
    determine a time-averaged mean position of the target; and
    calculate a treatment plan in which the source of therapeutic radiation is directed at the time-averaged mean position of the target, and in which the source of therapeutic radiation is gated to deliver radiation only when the target is within a treatment volume centred on the time-averaged mean position, the treatment volume having a dimension smaller than the magnitude of the cyclical motion.

12. The computer program product as claimed in claim 11, wherein the relevant dimension is equal to the diameter of the target plus a safety margin.

13. The computer program product as claimed in claim 12, wherein the safety margin is at most 15 mm.

14. The computer program product as claimed in claim 13, wherein the safety margin is at most 10 mm.

* * * * *